US00PP20199P3

(12) United States Plant Patent
Lin

(10) Patent No.: US PP20,199 P3
(45) Date of Patent: Aug. 4, 2009

(54) ***PHALAENOPSIS* PLANT NAMED 'SUNRISE CRYSTAL'**

(50) Latin Name: ***Phalaenopsis* sp.**
Varietal Denomination: Sunrise Crystal

(75) Inventor: Hou-Chih Lin, Taipei (TW)

(73) Assignee: Royal Base Corporation, Taipei (TW)

( * ) Notice: Subject to any disclaimer, the term of this patent is extended or adjusted under 35 U.S.C. 154(b) by 0 days.

(21) Appl. No.: 11/905,454

(22) Filed: Oct. 1, 2007

(65) Prior Publication Data

US 2009/0089906 P1 Apr. 2, 2009

(51) Int. Cl.
*A01H 5/00* (2006.01)

(52) U.S. Cl. ..... Plt./311
(58) Field of Classification Search ..... Plt./311
See application file for complete search history.

(56) References Cited

PUBLICATIONS

New Orchid Hybrids; The Royal Horticultural Society as International Cultivar Registration Authority for Orchid Hybrids, May–Jul. 2003 (17 pages total).*

* cited by examiner

*Primary Examiner*—Susan B McCormick Ewoldt
(74) *Attorney, Agent, or Firm*—Muncy, Geissler, Olds & Lowe, PLLC

(57) ABSTRACT

A new and distinct *Phalaenopsis* orchid plant named 'Sunrise Crystal' particularly characterized by its attractive and unique white-colored flowers with red purple-colored stripes and red purple-colored labellum and economical propagation via tissue culture. 'Sunrise Crystal' has upright, freely branching, sturdy flowering stems. 'Sunrise Crystal' has excellent postproduction longevity, a rapid growth rate, and a compact plant structure which suitable for packaging and shipping to the market.

2 Drawing Sheets

Botanical classification: *Phalaenopsis* sp.
Variety denomination: 'Sunrise Crystal'.

The present invention relates to botanical classification/cultivar designation: *Phalaenopsis* Orchid cultivar Sunrise Crystal.

BACKGROUND OF THE INVENTION

The present invention comprises a new and distinct cultivar of *Phalaenopsis* Orchid, hereinafter referred to by the cultivar name, Sunrise Crystal.

The new cultivar is a product of a planned breeding program conducted by the inventor in Taiwan. The objective of the breeding program is to create new uniform pot-type *Phalaenopsis* Orchid cultivars having attractive flower coloration.

The new cultivar breeder was Hou-Chih Lin. The new cultivar was discovered by the inventor from within the progeny of a cross-pollination of two identified proprietary selections of *Phalaenopsis* Orchid, not patented, on Apr. 19, 1999, in a controlled environment in Taiwan. Later, it was verified and registered in Royal Horticulture Society (R.H.S.) and had its variety name "*P.* Sunrise Crystal" on June, 2003.

Asexual propagation by tissue culture in a laboratory in Taiwan has been used to increase the number of plants for evaluation and has demonstrated that the unique combination of characteristics as herein disclosed for the new *Phalaenopsis* Orchid are firmly fixed and are retained through successive generations of asexual reproduction.

SUMMARY OF THE INVENTION

The following traits have been repeatedly observed and are determined to be basic characteristics which, in combination, distinguish this *Phalaenopsis* Orchid as a new and distinct cultivar:

1. Petal having a white main color and striped color pattern.
2. White-colored flowers with red purple-colored stripes and red purple-colored labellum.
3. Freely flowering habit.
4. Upright, freely branching and sturdy flowering stems.
5. Excellent postproduction longevity.

Plants of the new cultivar differ primarily from plants of the parent cultivars in flower color.

Plants of the new *Phalaenopsis* Orchid can be compared to plants of the cultivar *P.* Brother Girl (not patented), differing from plants of the cultivar *P.* Brother Girl in the following characteristics:

1. Plants of the new *Phalaenopsis* Orchid are smaller than plants of the cultivar *P.* Brother Girl.
2. Plants of the new *Phalaenopsis* Orchid are more freely flowering than plants of the cultivar *P.* Brother Girl.
3. Plants of the new *Phalaenopsis* Orchid have more branches in inflorescence with more flowers per inflorescence than plants of the cultivar *P.* Brother Girl.
5. Plants of the new *Phalaenopsis* Orchid have smaller flowers than plants of the cultivar *P.* Brother Girl.
6. Plants of the new *Phalaenopsis* Orchid and the cultivar *P.* Brother Girl differ in labellum color. The former is red purple-colored and the latter is dark red purple-colored.

BRIEF DESCRIPTION OF THE DRAWINGS

Colors in the photographs may appear different from the color values that appear in the detailed botanical description which more accurately describe the new cultivar.

DETAILED DESCRIPTION OF THE PREFERRED EMBODIMENTS

Figure 1:
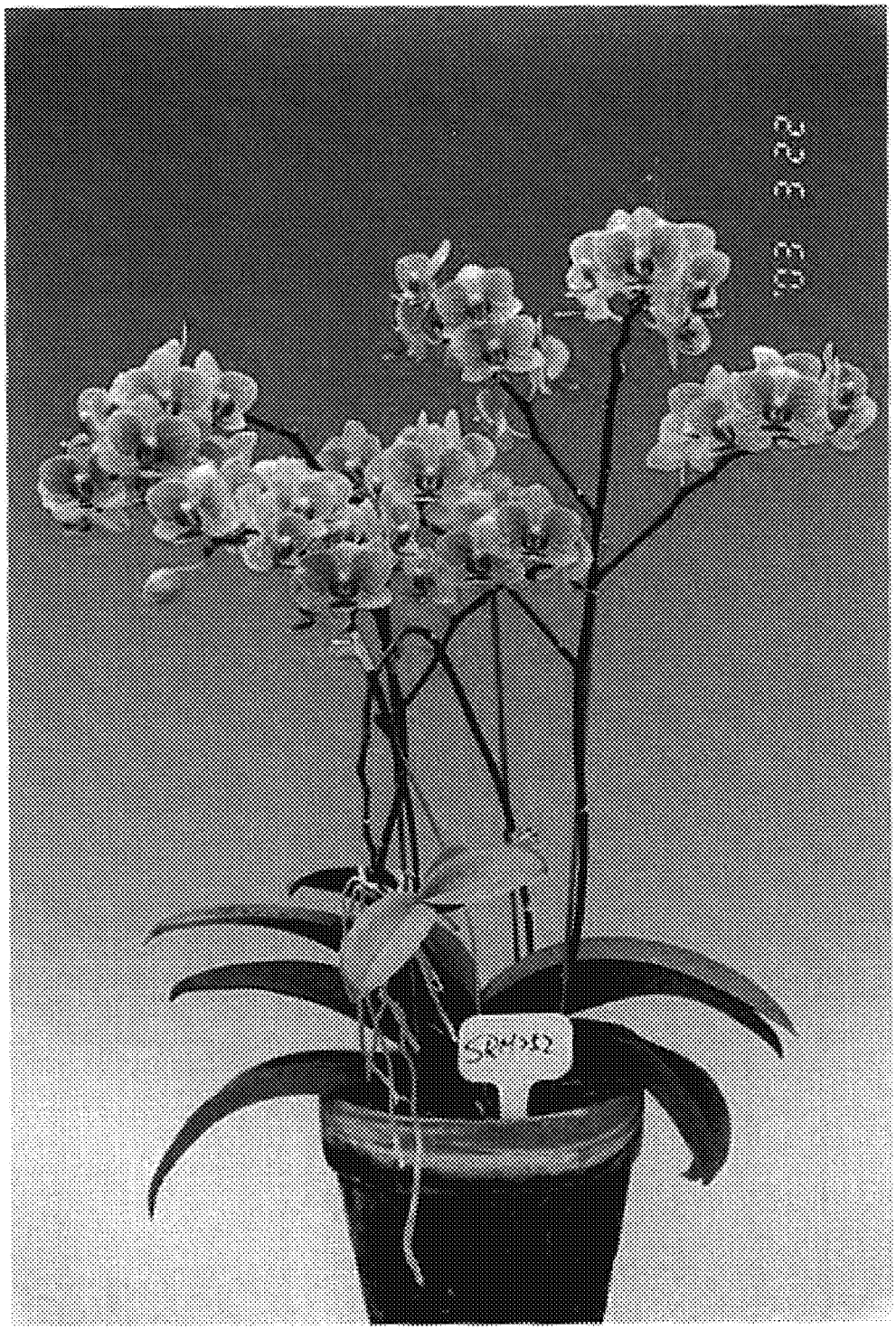
FIG. 1 is a side view of a plant of 'Sunrise Crystal' flowering in a 12 cm pot.
Figure 2:
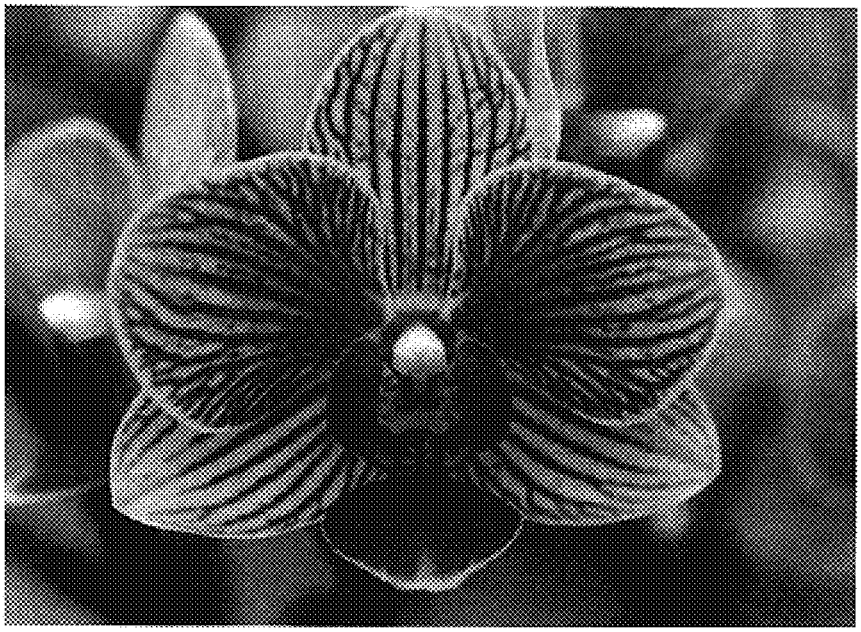
FIG. 2 is a close-up view showing the characteristics of the flower.
Figure 3:
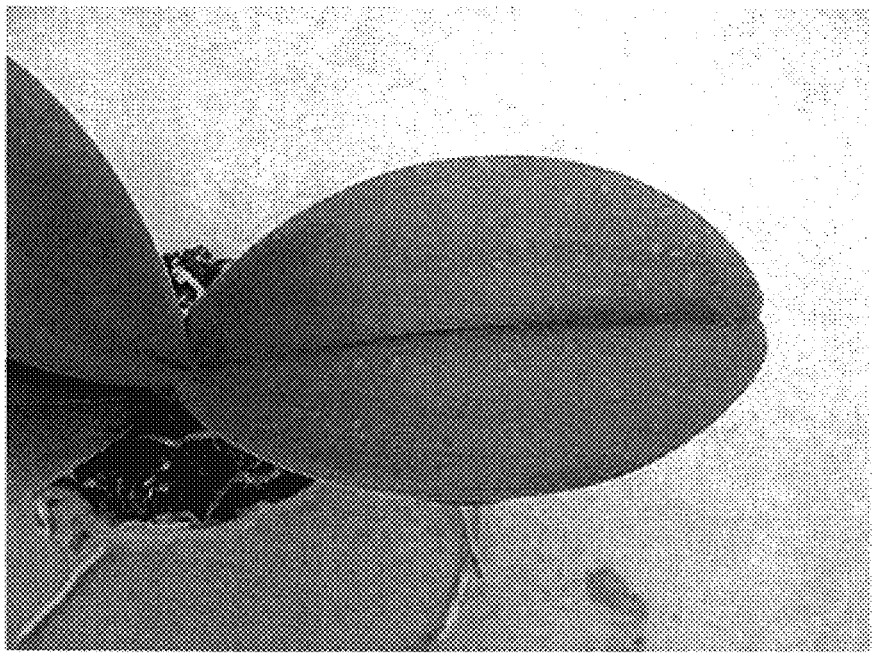
FIG. 3 is a close-up view showing the characteristics of the leaf.

Plants of the new cultivar have not been observed under all possible environmental conditions. The phenotype may vary significantly with variations in environment such as temperature and light intensity, without however, any change in genotype. In the following description, color references are made to The Royal Horticultural Society Colour Chart, 1995 Edition, except where general terms of ordinary dictionary significance are used.

Plants used for the aforementioned photographs and following detailed botanical description were 14 months old and grown in 12-cm containers in Taiwan, in a greenhouse with day temperatures about 25 to 28° C., night temperatures about 18 to 20° C., and light levels about 16,000 to 28,000 lux. The photographs and the detailed botanical description were taken during the winter.

Parentage:
- *Seed.*—*P.* Golden Sun., not patented.
- *Pollen.*—*P.* Carmela's Pixie, not patented.

Propagation: Asexual propagation by tissue culture.

Root description: Very thick, fleshy, and greenish white in color.

Plant shape: Two-ranked leaves affixed to a short central stem (monopodial growth). Single flowers arranged on upright and sturdy flowering compound racemes.

Plant height, soil level to top of foliar plane: About 12 to 14 cm.

Plant height, soil level to top of inflorescences: About 40 to 50 cm.

Plant diameter: About 25 to 30 cm.

Flowers per stem: Approximately 20 to 40.

Foliage description:
- *Leaves.*—Simple, opposite, sessile.
- *Quantity per plant.*—About 5 to 6.
- *Length.*—About 16 to 20 cm.
- *Width.*—About 8 to 10 cm.
- *Shape.*—Elliptic.
- *Apex.*—Obtuse.
- *Base.*—Cuneate.
- *Margin.*—Entire.
- *Aspect.*—Mostly flat and folded upward from the midrib.
- *Texture, upper and lower surfaces.*—Leathery, thick, glabrous.
- *Venation.*—Parallel.
- *Color* (*upper surface*).—RHS 137A.
- *Color* (*lower surface*).—RHS 141C.

Flower description:
- *Flower type.*—Single zygomorphic flowers, roughly pentagonal in shape.
- *Flower arrangement.*—Compound racemes.
- *Flowering stems.*—Upright, freely branching and sturdy.
- *Flowering habit.*—Plants freely flowering; plants typically produce two to three branched flowering stems with at least 20 to 25 flowers each.
- *Fragrance.*—Flowers not fragrant.
- *Self cleaning or persistent.*—Flowers persistent.
- *Flower aspect.*—Flowers facing mostly outward.
- *Natural flowering season.*—From January to April in Taiwan. Plants begin flowering about $14^{th}$ months after planting.
- *Post-production longevity.*—Plants of the new *Phalaenopsis* Orchid maintain good leaf and flower substance for about three to six months on the plant under interior environmental conditions. Cut flowers of the new *Phalaenopsis* Orchid maintain good substance for about three to four weeks.
- *Inflorescence length.*—About 30 to 40 cm.
- *Inflorescence diameter.*—About 25 to 30 cm.
- *Flower bud* (*just before anthesis*).—Flower bud shape. — bullet-like. Flower bud length. — About 1.7 cm. Flower bud diameter. — About 1.2 cm. Flower bud color. — About RHS74A.
- *Flower diameter.*—About 6 to 6.5 cm.
- *Flower depth.*—About 1.4 to 1.8 cm.
- *Number of petals.*—Two per flower.
- *Petal size.*—Lateral petals similar in size and shape.
- *Length.*—About 3.1 cm.
- *Diameter.*—About 3 cm.
- *Shape.*—Ovate.
- *Apex.*—Rounded.
- *Base.*—Attenuate; fused with the column.
- *Margin.*—Entire.
- *Texture, upper and lower surfaces.*—Velvety, smooth.
- *Color.*—When blossoming, the main color of the adaxial surface of the petal is white (RHS155A) with purple-colored stripes (RHS78B), stretching along the veins. The main color of the abaxial surface of the petal is white (RHS155A).

Labellum:
- *Length, not flattened.*—About 2.1 cm.
- *Diameter, not flattened.*—About 1.8 cm.
- *Shape.*—Deeply three-lobed with two prominent callosities on the upper surface at the central junction of the lateral lobes and base of the midlobe. The lateral lobes fold upward about the column, extend forward and are terminated by two twisted filiform appendages (about 5 mm in length) at the apex.
- *Base color of the abaxial surface of the apical lobe.*—Purple (RHS71A).
- *Tip color of the adaxial surface of the apical lobe.*—Purple (RHS74B).

Sepals:
- *Quantity.*—Three per flower.
- *Dorsal sepal length.*—About 3.1 cm.
- *Lateral sepal length.*—3.5 cm.
- *Dorsal sepal diameter.*—About 2.3 cm.
- *Lateral sepal diameter.*—About 2.5 cm.
- *Shape.*—Ovate.
- *Apex.*—Rounded acute to retuse.
- *Base.*—Attenuate; fused with the petals and column.
- *Margin.*—Entire.
- *Texture, upper and lower surfaces.*—Velvety; smooth.
- *Dorsal sepal main color.*—RHS 155B, with purple streaks RHS 78A.
- *Dorsal sepal pattern color.*—RHS 78A.
- *Lateral sepal main color.*—11D light yellow; towards the base, 155A with purple, 78A, streaks and stripes along the veins.
- *Lateral sepal pattern color.*—RHS 78B.

Peduncles:

*Length.*—About 25 to 35 cm.

*Diameter.*—About 6 mm.

*Aspect.*—Upright.

*Strength.*—Strong, sturdy.

*Texture.*—Smooth, glabrous.

*Color.*—RHS 187B.

Pedicels:

*Length.*—About 10 to 15 cm.

*Diameter.*—About 3 to 4 mm.

*Aspect.*—About 65 from vertical.

*Strength.*—Strong.

*Texture.*—Smooth, glabrous.

*Color.*—RHS 187B.

*Color towards the base.*—RHS 187B.

Reproductive organs: The stamens, style and stigmas are fused into a single, short structure called the column, possessing one terminal anther with pollen grains united into a pollinia, which are covered by an anther cap. The stigma is located under the column behind the pollinia. The ovary is inferior with three carpels presented. The plant has not produced seed.

*Column.*—Length. — About 1.1 cm. Diameter. — About 3 to 4 mm. Color. — RHS 155C. Color towards to apex. — RHS 74C.

*Pollinia.*—Quantity of pollen masses. — Two pollen masses. Diameter. — About 1 mm. Color. — RHS 25A.

Ovary. —Length. — About 3.7 to 3.9 mm. Diameter. — About 3 to 5 mm. Color. — RHS 155C.

*Root.*—In tissue culture plantlets, the first root emerged 30 days after being deflasked. Diameter. — About 3 to 5 mm. Color. — RHS 144A.

Disease/pest resistance: Resistance to known pathogens and pests common to *Phalaenopsis* Orchids has not been observed on plants of the new cultivar grown under commercial greenhouse conditions.

Temperature tolerance: Plants of the new *Phalaenopsis* orchid have been observed to be tolerant to temperatures from about 14 to 32° C.

What is claimed is:

1. A new and distinct cultivar of *Phalaenopsis* plant named 'Sunrise Crystal', as illustrated and described.

* * * * *